United States Patent
Maruo et al.

(10) Patent No.: US 7,056,527 B2
(45) Date of Patent: Jun. 6, 2006

(54) PATCHES CONTAINING BUPRENORPHINE HYDROCHLORIDE

(75) Inventors: Susumu Maruo, Tokyo (JP); Osafumi Hidaka, Tokyo (JP); Satoshi Murakami, Tokyo (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/959,117

(22) PCT Filed: Feb. 22, 2001

(86) PCT No.: PCT/JP01/01293

§ 371 (c)(1), (2), (4) Date: Oct. 19, 2001

(87) PCT Pub. No.: WO01/62254

PCT Pub. Date: Aug. 30, 2001

(65) Prior Publication Data

US 2002/0182247 A1    Dec. 5, 2002

(30) Foreign Application Priority Data

Feb. 25, 2000    (JP) .............................. 2000-049298

(51) Int. Cl.
*A61K 9/00* (2006.01)
*A61K 9/70* (2006.01)
*A61F 13/00* (2006.01)
*A61F 13/02* (2006.01)

(52) U.S. Cl. ...................... 424/447; 424/400; 424/443; 424/448; 424/449; 424/484; 424/486; 424/487

(58) Field of Classification Search ................. 424/400, 424/448, 449, 484, 486, 487, 443, 447
See application file for complete search history.

(56) References Cited

U.S. PATENT DOCUMENTS

| 4,879,297 A | | 11/1989 | Mahjour et al. |
| 5,176,916 A | * | 1/1993 | Yamanaka et al. |
| 6,264,980 B1 | | 7/2001 | Hille |

FOREIGN PATENT DOCUMENTS

| DE | 4446600 A | 6/1996 |
| EP | 0 432 945 A1 | 6/1991 |
| JP | 04-103528 A | 4/1992 |
| JP | 04-217926 A | 8/1992 |
| JP | 07-010754 A | 1/1995 |
| JP | 07-304672 A | 11/1995 |
| JP | 10-045571 A | 2/1998 |
| WO | WO 88/09676 | 12/1988 |
| WO | WO 93/08841 | 5/1993 |

OTHER PUBLICATIONS

XP 002235231, Apr. 6, 1992, Sekisui Chem Ind. Co Ltd.
XP 002235232, Jan. 13, 1995, Sekisui Chem Ind Co Ltd.

* cited by examiner

*Primary Examiner*—Thurman K. Page
*Assistant Examiner*—Simon J. Oh
(74) *Attorney, Agent, or Firm*—Sughrue Mion, PLLC

(57) ABSTRACT

A patch comprising an adhesive layer formed on one surface of a flexible support, wherein said adhesive layer containing a drug, an absorption enhancer and an adhesive comprising; (i) said drug is buprenorphine hydrochloride and/or buprenorphine, and (ii) said absorption enhancer is a mixture of polyoxyethylene sorbitan mono fatty acid ester having 6 to 20 of oxyethylene units and 12 to 18 of carbon number of fatty acid ester, and at least one selected from the group consisting of liquid higher fatty acid ester, 60 to 180 of molecular weight of liquid poly hydric alcohol, lactic acid and triacetin, and (iii) said adhesive is an acrylic-based adhesive.

1 Claim, No Drawings

PATCHES CONTAINING BUPRENORPHINE HYDROCHLORIDE

TECHNICAL FIELD

This invention relates to a patch containing buprenorphine hydrochloride and/or buprenorphine.

BACKGROUND ART

Cancer represents the most frequent cause of death in Japanese. Lots of cancer patients have cancer pain. Therefore, to relieve the cancer pain is very important and to treat cancer is also. Because of the nonnarcotic, buprenorphine is very useful as a drug for pain relief of all others. And buprenorphine is put into practice as injection or suppository. In the above-mentioned administration method, however, patients have a pain or discomfort. Therefore, in recent years, percutaneous administration by patches has been studied in order to dissolve the pain or the discomfort. Patches increased drug permeability by using various absorption enhancers are disclosed (for example, Unexamined patent publication JP 4-217926, Unexamined patent publication JP 7-10754, Unexamined patent publication JP 7-304672, Published Japanese translation of PCT JP 10-512551). The patches disclosed in the above documents are improved in terms of drug permeability, but they are not yet satisfied in terms of safety or economical reasons.

DISCLOSURE OF INVENTION

The object of this invention is to provide a buprenorphine hydrochloride and/or buprenorphine patch having advantages with respect to drug permeability, safety and economy. The present inventors have intensively researched to solve the above-mentioned problems. As a result, it has been found that the patch comprising a drug, a specific absorption enhancer and an adhesive is satisfied with the object of the present invention, and consequently we have achieved the present invention.

Namely, this invention provides a patch comprising an adhesive layer formed on one surface of a flexible support, wherein said adhesive layer containing a drug, an absorption enhancer and an adhesive comprising;
(i) said drug is buprenorphine hydrochloride and/or buprenorphine, and
(ii) said absorption enhancer is a mixture of polyoxyethylene sorbitan mono fatty acid ester having 6 to 20 of oxyethylene units and 12 to 18 of carbon number of fatty acid ester, and at least one selected from the group consisting of liquid higher fatty acid ester, 60 to 180 of molecular weight of liquid poly hydric alcohol, lactic acid and triacetin, and
(iii) said adhesive is an acrylic-based adhesive.

BEST MODE FOR CARRYING OUT THE INVENTION

The absorption enhancer of this invention is a mixture of (a) polyoxyethylene sorbitan mono fatty acid ester having 6 to 20 of oxyethylene units and 12 to 18 of carbon number of fatty acid ester and (b) at least one type of compound selected from the group consisting of liquid higher fatty acid ester, liquid poly hydric alcohol of which the molecular weight is 60 to 180, lactic acid and triacetin.

The polyoxyethylene sorbitan mono fatty acid esters of this invention is having 6 to 20 of oxyethylene units and 12 to 18 of carbon numbers of fatty acid ester. The polyoxyethylene sorbitan mono fatty acid ester having except 6 to 12 of oxyethylene units is not preferable, because of less permeability and cost. In addition, the polyoxyethylene sorbitan mono fatty acid ester having except 12 to 18 of carbon numbers is not preferable, because of safety to living body or economical reasons. As examples of the polyoxyethylene sorbitan mono fatty acid ester in this invention are polyoxyethylene (20) sorbitan mono laurate, polyoxyethylene (20) sorbitan mono palmitate, polyoxyethylene (6) sorbitan mono stearate, polyoxyethylene (20) sorbitan mono stearate, and polyoxyethylene (20) sorbitan mono oleate. In the above-mentioned polyoxyethylene mono fatty acid esters, polyoxyethylene (20) sorbitan mono oleate is especially preferable in terms of its skin permeability of the drug.

As the liquid higher fatty acid esters having 12 to 18 carbon numbers in the present invention include such as isopropyl myristate, isopropyl palmitate, isostearyl palmitate, ethyl oleate, decyl oleate and hexyl laurate. In above mentioned liquid higher fatty acid esters, isopropyl myristate is more preferable in terms of drug permeability, skin irritation and economical reasons.

The liquid poly hydric alcohol of which the molecular weight is 60 to 180 in the present invention include glycerin, propylene glycol, butanediol and hexanetriol. Hexanetriol or propylene glycol is more preferable in terms of drug permeability.

In the present invention, it is important that the absorption enhancer is a mixture of polyoxyethylene sorbitan mono fatty acid ester and at least one selected from the group consisting of higher fatty acid ester, polyhydric alcohol, lactic acid and triacetin. In case the absorption enhancer is polyoxyethylene sorbitan mono fatty acid ester alone or in case the absorption enhancer is at least one selected from the group consisting of higher fatty acid ester, polyhydric alcohol, lactic acid and triacetin, the drug permeability will be not enough.

Namely, polyoxyethylene sorbitan mono fatty acid ester is essential component as the absorption enhancer of this invention.

The amount of polyoxyethylene sorbitan mono fatty acid ester in the present invention is 1 to 20% by weight based on the total weight of the adhesive layer, more preferably 2 to 10% by weight based on the total weight of the adhesive layer. In case the amount of the absorption enhancer is less than 1% by weight based on the total weight of the adhesive layer, the improvement of increasing drug permeability is difficult. On the other hand, in case the amount of absorption enhancer exceeds 20% by weight based on the total weight of the adhesive layer, the effect on increasing drug permeability reaches the ceiling. Therefore it is not proper in terms of economical reasons.

Moreover, the amount of an absorption enhancer selected from the group consisting of higher fatty acid ester, polyhydric alcohol, lactic acid and triacetin is 5 to 49% by weight based on the total weight of the adhesive layer. Preferably, the amount of the above mentioned absorption enhancer is 8 to 35% by weight based on the total weight of the adhesive layer. When the amount is less than 5% by weight, the cutaneous absorption of the drug sometimes becomes inadequate. When the amount exceeds 49% by weight, part of the adhesive layer of the patch sometimes remains on the skin after peeling the patch off the skin.

In addition, the amount of the mixture of polyoxyethylene sorbitan mono fatty acid ester and at least one selected from the group consisting of higher fatty acid ester, poly hydric alcohol, lactic acid and triacetin is 6 to 50% by weight based on the total weight of the adhesive layer. Preferably the above-mentioned amount is 10 to 40% by weight. The patch having less than 6% by weight of the absorption enhancer is nor preferable, because the cutaneous absorption of the drug is not sufficient. The patch having more than 50% by weight of the absorption enhancer is not preferable, because part of the adhesive layer of the patch sometimes remains on the skin after peeling the patch off the skin.

The acrylic-based adhesive of this invention preferably comprises alkyl (meth)acrylate having 2 to 20 carbon numbers as a base component and having less than 10% by weight of acrylic acid. Examples of alkyl (meth) acrylate having 2 to 20 carbon atoms include ethyl (meth) acrylate, butyl (meth) acrylate, pentyl (meth) acrylate, hexyl (meth) acrylate, heptyl (meth) acrylate, octyl (meth) acrylate, 2-ethylhexyl (meth) acrylate, nonyl (meth) acrylate, hexadecyl (meth) acrylate and dodecyl (meth) acrylate. In particular, copolymers having 2-ethylhexyl (meth) acrylate as their main component are more preferable in terms of adhesion. Moreover, it is possible to mix polyvinyl acetate-based adhesive or silicone-based adhesive less than 50 wt % with the polyacrylate ester-based adhesive in order to adjust the adhesion.

The drug in the present invention is buprenorphine hydrochloride or buprenorphine or the mixture of them. The amount of buprenorphine hydrochloride and/or buprenorphine is not especially limited. Preferably, the above-mentioned amount is 3 to 20% by weight, more preferably 7 to 15% by weight.

Forms of the patch in the present invention include known forms. Examples of the form include monolithic-type patch in which a drug and an absorption enhancer are contained one adhesive layer; reservoir-type patch consisting of a drug reservoir layer, which contain a drug and an absorption enhancer, and an adhesive layer to be attached on the skin; and multilaminate-type patch formed by laminating several layers which contain different content of a drug and an absorption enhancer each other. In terms of economic reasons, the monolithic-type patch is more preferred.

In addition, as means of containing pharmaceutical preparation, a pharmaceutical solution may be mixed in advance into an adhesive, and this mixed solution may be coated onto a support to form a self-adhesive layer containing pharmaceutical, or an amount of pharmaceutical preparation sufficient for transcutaneous absorption may be contained in a self-adhesive layer either not containing pharmaceutical preparation or containing an insufficient amount of pharmaceutical preparation by a method such as impregnation, contact transfer or spraying. A suitable method can be selected and employed from known methods corresponding to the physical properties and so forth. According to physical property of the drug, ordinary method such as, for example, above-mentioned method can be used.

Moreover, alkali such as sodium hydroxide or potassium hydroxide can be added to improve the drug solubility in the adhesive layer.

Also the adhesive can be crosslinked by an ordinary method in order to increase cohesion of the adhesive layer. As the crosslinking method, irradiation of ultraviolet ray or gamma ray can be used, besides the crosslinking agent such as polyisocyanate compound, silicic acid anhydride, organometallic salt or metallic chelate compound can be used.

Furthermore, ordinary stabilizing agent, antioxidant, flavor, preservative or pH adjusting agent can be added to the patch of the present invention. Specifically, stabilizing agents such as, for example, magnesium stearate, zinc stearate or citric acid anhydride; antioxidants such as ascorbic acid, tocopherol acetate or vitamin E; flavor such as, for example, menthol, camphor, peppermint oil or lemon oil; preservatives such as, for example, dibutyl hydroxy toluene or isobutyl paraoxy benzoate; pH adjusting agent such as, for example, sodium citrate, monobasic sodium citrate, dibasic sodium phosphate or monobasic sodium phosphate can be used. The above-mentioned substances can be used by itself or as a mixture of one, two or more of them.

The flexible support of this invention is not particularly limited in its materials or its forms. The support should allow the adhesive layer to stick it. Further the support has self-shape retention. The support of this invention can be selected from, for example, polymer films such as polyester, polyolefin, polyurethane or cellulose ester; woven fabrics, knitted fabrics, unwoven fabrics or papers such as polyester, polyolefin, polyurethane, cellulose ester or polyamide; porous membranes such as polyester, polyolefin, polyurethane, cellulose ester or polyamide; and laminate comprising a combination of two or more of the above-mentioned materials. Though thickness of the support of this invention is not particularly limited, 100 to 2000 μm is preferable, and 200 to 1000 μm is more preferable.

Thickness of the adhesive layer of this invention is not particularly limited, 5 to 200 μm is preferable, and 10 to 100 μm is more preferable.

As mentioned above, the patch comprising buprenorphine (hydrochloride), the acrylic-based adhesive and the absorption enhancer, and having an excellent permeability of buprenorphine hydrochloride and/or buprenorphine, safety and economy can be provided by using the mixture of polyoxyethylene mono fatty acid and one selected from the group consisting of higher fatty acid ester, poly hydric alcohol, lactic acid and triacetin as the absorption enhancer.

EXAMPLES

Hereinafter this invention is explained by examples. In the examples, 'parts' and '%' refer to 'parts by weight' and '% by weight' respectively. Further in the examples, percentage of drug permeation was calculated by measuring the amount of drug in the patch by means of high performance liquid chromatography before and 24 hours after application of the patch on the back of hairless rat.

Example 1

1.1 parts of buprenorphine hydrochloride, 0.25 parts of polyoxyethylene sorbitan mono oleate, 1.0 parts of isopropyl myristate, 0.07 parts of sodium hydroxide, 0.1 parts of magnesium stearate, 86 parts of ethyl acetate, 30 parts of ethanol and 4 parts of methanol were added to alkyl polyacrylate ester copolymer solution, as the polyacrylate ester-based adhesive, comprising 90% of 2-ethylhexylacrylate, 7.5% of methyl methacrylate and 2.5% of acrylic acid. Subsequently, the obtained solution was coated on the silicon-coated mold release film so that the thickness of the adhesive layer after drying was 10 μm followed by drying for 30 minutes at 60 degrees C. 3.5 μm PET film was affixed on the upper surface of the resulting adhesive layer to prepare the patch. The obtained patch was cut into pieces measuring Φ 18 mm, the cut patch has been applied on depilated back of hairless rat for 24 hours. Percentage of drug permeation was calculated by measuring the amount of drug in the patch by means of high performance liquid chromatography before and 24 hours after application of the patch on the back of hairless rat. The results were shown in Table 1. As shown in Table 1, the patch showed high permeability.

Examples 2 to 8, Comparative Examples 1 to 3

The patch was give by the same way as Example 1. However the compound compositions were changed as showed in Table 1.

As shown in Table 1, patches of Example 2 to 8 showed high permeability of the drug. On the other hand, the patch of comparative examples 1 and 2 contained polyoxyethylene sorbitan mono oleate only or isopropyl myristate only showed the insufficient drug permeation. Moreover, as shown in table 1, in comparative example 3, the drug permeability was not enough in case the patch contained no absorption enhancer.

TABLE 1

|  | Ex. 1 | Ex. 2 | Ex. 3 | Ex. 4 | Ex. 5 | Ex. 6 | Ex. 7 | Ex. 8 | C. Ex. 1 | C. Ex. 2 | C. Ex. 3 |
|---|---|---|---|---|---|---|---|---|---|---|---|
| buprenorphine hydrochrolide | 11 | 12 | 11 | 11 | 11 | 11 | 12 | 12 | 12 | 12 | 12 |
| acrylic-based adhesive | 76.5 | 73 | 76.5 | 76.5 | 76.5 | 76.5 | 68 | 53 | 78 | 83 | 88 |
| polyoxyethylene(20) sorbitan mono oleate | 2.5 | — | 2.5 | 2.5 | 2.5 | 2.5 | 10 | 5 | — | 5 | — |
| polyoxyethylene(20) sorbitan mono stearate | — | 5 | — | — | — | — | — | — | — | — | — |
| isopropyl myristate | 10 | 10 | — | — | — | — | 10 | 30 | 10 | — | — |
| glycerin | — | — | 10 | — | — | — | — | — | — | — | — |
| 1,2,6-hexan triol | — | — | — | 10 | — | — | — | — | — | — | — |
| triacetin | — | — | — | — | 10 | — | — | — | — | — | — |
| lactic acid | — | — | — | — | — | 10 | — | — | — | — | — |
| amount of drug permeation (%) | 35.6 | 24.7 | 31.8 | 25.3 | 38.2 | 42.4 | 41.2 | 57.5 | 13.3 | 9.3 | 14.9 |

The invention claimed is:

1. A patch comprising an adhesive layer formed on one surface of a flexible support, wherein said adhesive layer consists essentially of a drug, an absorption enhancer and an adhesive wherein:
   (i) said drug is buprenorphine hydrochloride and/or buprenorphine, and
   (ii) said absorption enhancer consists essentially of a mixture of polyoxyethylene mono fatty acid ester having 6 to 20 of oxyethylene units and 12 to 18 of carbon number of fatty acid ester,
   and at least one selected from the group consisting of liquid higher fatty acid ester, 60 to 180 of molecular weight of liquid poly hydric alcohol, lactic acid and triacetin, and
   (iii) said adhesive is an acrylic-based adhesive,
   wherein the amount of the polyoxyethylene mono fatty acid ester is 1 to 20% by weight based on the total weight of the adhesive layer,
   the amount of at least one component selected from the group consisting of higher fatty acid ester, poly hydric alcohol, lactic acid and triacetin is 5 to 49% by weight based on the total weight of the adhesive layer,
   and the total amount of the absorption enhancer mixture is 6 to 50% by weight based on the total weight of the adhesive layer.

* * * * *